United States Patent [19]

Sandhu

[11] 4,379,408
[45] Apr. 12, 1983

[54] LIQUID CRYSTAL TECHNIQUE FOR EXAMINING INTERNAL STRUCTURES

[75] Inventor: Jaswinder S. Sandhu, Chicago, Ill.

[73] Assignee: Raj Technology Partnership, Chicago, Ill.

[21] Appl. No.: 232,247

[22] Filed: Feb. 6, 1981

Related U.S. Application Data

[63] Continuation-in-part of Ser. No. 224,173, Jan. 12, 1981.

[51] Int. Cl.³ .......................... G01N 29/00; G02F 1/11
[52] U.S. Cl. ........................................ 73/603; 350/330
[58] Field of Search .................. 73/603, 604, 606, 655, 73/656; 350/330, 340, 342; 367/7, 8, 10

[56] References Cited

U.S. PATENT DOCUMENTS

| | | | |
|---|---|---|---|
| 3,597,043 | 8/1971 | Dreyer | 350/330 |
| 3,831,434 | 8/1974 | Greguss | 73/603 |
| 3,984,343 | 10/1976 | Cole, Jr. et al. | 350/330 |
| 3,991,606 | 11/1976 | Dreyer | 73/603 |
| 4,338,821 | 7/1982 | Dion | 73/603 |

OTHER PUBLICATIONS

P. Greguss, "A New Liquid Crystal Acoustical-To-Optical Display," *Acustica*, vol. 29, pp. 52–58, 1973.
R. Bartolino et al., "Ultrasonic Modulation of Light with a Liquid Crystal in the Smectic-A and Nematic Phases", *J. of Applied Physics*, vol. 46, No. 5, pp. 1928–1933, May 1975.
S. Nagai et al., "Acousto-Optical Effects in a Nematic Liquid Crystal", *Revue De Physique Appliquee*, vol. 12, No. 1, pp. 21–30, Jan. 1977.

*Primary Examiner*—Stephen A. Kreitman
*Attorney, Agent, or Firm*—Gerald S. Geren

[57] ABSTRACT

There is disclosed herein an ultrasonic system for detecting internal discontinuities in a body. The system includes: an ultrasonic transducer for directing sonic energy toward a body; a liquid crystal, acousto-optical detector cell for detecting ultrasonic energy passing through said body; an optical system for illuminating said liquid crystal cell; and a liquid medium for coupling the transducer body and cell.

The acousto-optical cell includes a pair of substantially rigid covers, a liquid crystal material positioned between said covers and a peripheral spacer and sealing member surrounding said liquid crystal and sealingly engaging said covers. Each of the covers is substantially acoustically transparent and at least one of said covers is optically transparent. The optically transparent cover is a laminate having at least three layers, with each of said layers of said laminate having a thickness much much less than ¼ of the wave length of the ultrasonic energy propagating through said layer. The other cover has at least one layer and the thickness of that layer is much much less than ¼ of the wave length of the ultrasonic energy propagating therethrough.

In this construction, it is essential that the acoustical impedance of the cell approximates the acoustical impedence of the coupling medium so as to minimize signal loss and image degradation. Furthermore, the liquid crystal material is usually of the nematic type and is homeotropically aligned.

23 Claims, 19 Drawing Figures

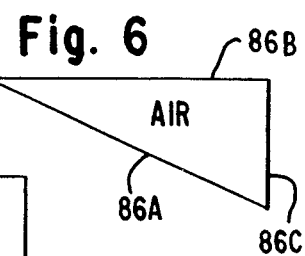
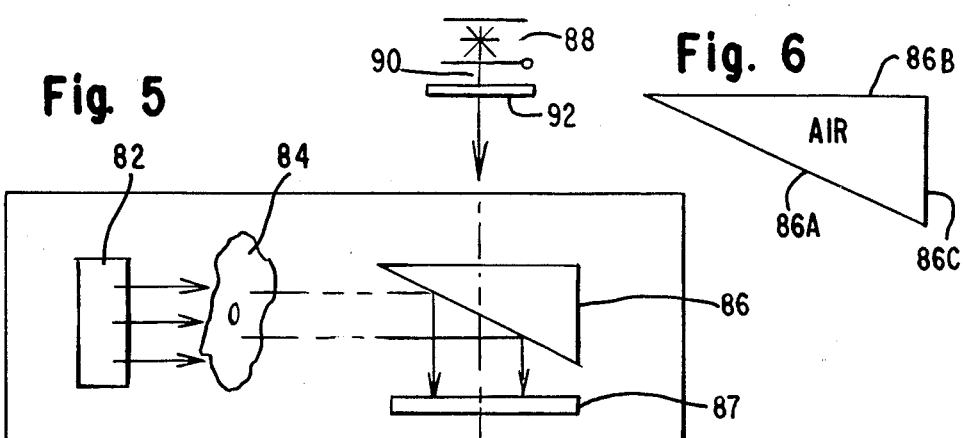
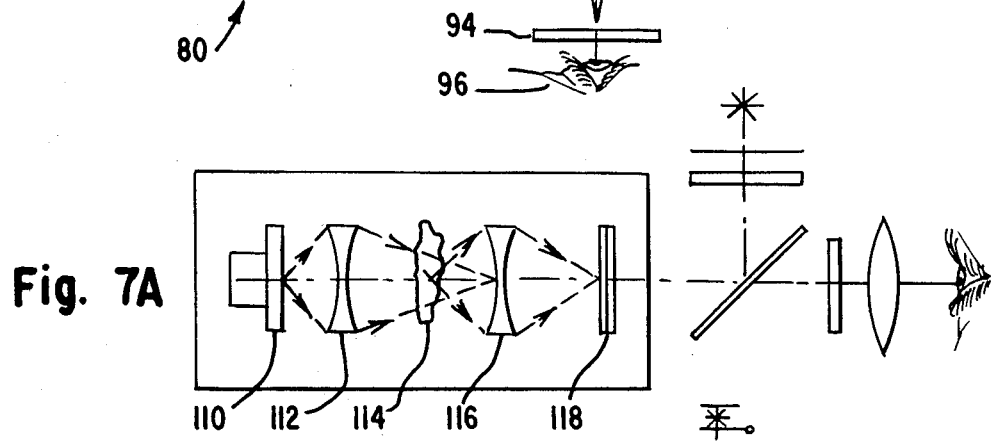
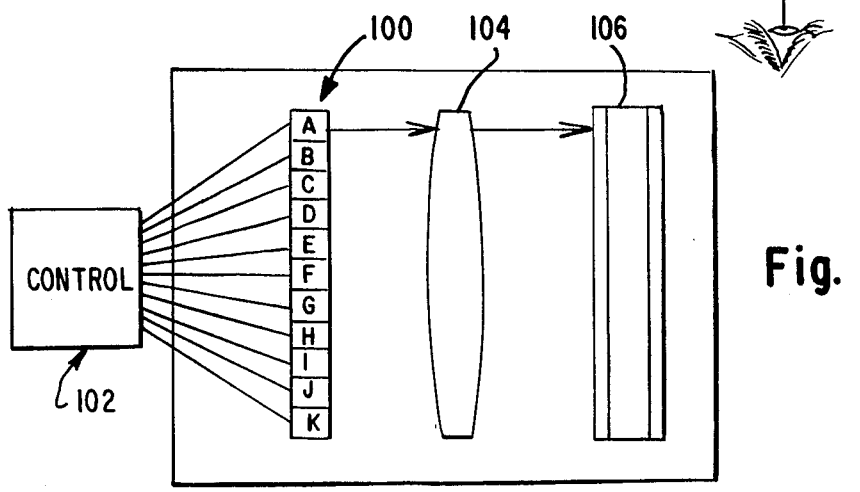

LIQUID CRYSTAL TECHNIQUE FOR EXAMINING INTERNAL STRUCTURES

CROSS REFERENCE TO RELATED APPLICATION

This application is a continuation-in-part of copending U.S. patent application, Ser. No. 224,173 filed Jan. 12, 1981.

BACKGROUND OF THE INVENTION

This invention relates to an apparatus and method for non-destructively inspecting various solid bodies, such as drill bits used in oil exploration, for internal flaws or discontinuities.

In many industrial situations it is desirable to inspect a part or tool for internal flaws or discontinuities before use. The purpose of such inspection is to minimize the possibility of failure during use, due to such flaws or discontinuities.

Such internal flaws may result from the processes by which the part is manufactured and may manifest themselves as cracks, non-metallic inclusions, or other similar internal discontinuities. When a workpiece is used and thus stressed, failure can initiate at the discontinuity.

This is particularly true in the exploration for oil where drill-bits can fail at thousands of feet below the surface. Such failures can be very expensive and are time-consuming to correct.

Obviously, destructive testing, such as sectioning for internal examination, is undesirable since the part is destroyed and no longer useful.

Non-destructive testing techniques are available and include: (1) x-ray analysis which is potentially hazardous and may require time-consuming development of negatives; and (2) ultrasonic testing wherein an emitting transducer and a receiving transducer are used—this is sometimes referred to as pulse-echo analysis. In order to achieve an acceptable image of a flaw using the pulse-echo technique, electronic or computer processing is required. Such processing requires expensive equipment, careful set-up and complicated signal processing, particularly where irregularly shaped bodies are to be inspected.

It is therefore an object of this invention to provide a non-destructive testing technique for use in detecting internal flaws or discontinuities in various solid bodies which does not have the hazards or problems of X-rays or the cost and inconvenience of electronic or computer-assisted imaging.

A particular object of this invention is to provide a technique for inspecting oil drill-bits.

Acoustical technology, more specifically, ultrasonic technology, is well known for non-destructively inspecting bodies for internal flaws. See, for example, Gooberman's text entitled *Ultrasonics Theory and Application*, published by E.U.P. Limited [11, "Miscellaneous Applications on Ultrasonics," subsection 1.2 "Flaw Detection." That text discloses and discusses the general principles of the use of ultrasonics in inspection techniques.

In an effort to eliminate some of the problems associated with the pulse-echo techniques, work has been done to employ liquid crystals as the detector or receiver of the ultrasonic signal so as to provide an inexpensive real time display of the flaws. Prior to the development disclosed herein the work done in the liquid crystal field did not provide for a suitable, economic and commercial liquid crystal device, generally because of very poor quality images.

Liquid crystals are elongated, organic molecules whose properties are anisotropic (i.e., not uniform in every direction). This characteristic permits the liquid crystals to be selectively excited so as to provide an informative display. There are three main types of thermotropic liquid crystals, namely smectic, nematic and cholesteric. A discussion of such liquid crystals is presented in a publication by E. Merck of Darmstadt, Germany, entitled "Licristal"—liquid crystals. Other references on liquid crystal materials are available, such as de Genness *Physics of Liquid Crystals*, Oxford University Press 1974 and S. Chandrasekar, *Liquid Crystals*, Cambridge University Press, 1978.

Liquid crystals have found extensive use in non-emissive electro-optical displays, e.g., timepieces, calculators, etc. This development has been possible due to unique physical properties, such as anisotropic dielectric constants, conductivities, etc.

A study, identified as "Acousto-Hydrodynamic Effects in Liquid Crystals" authored by J. S. Sandhu, W. G. B. Britton, and R. W. V. Stephens, Physics Department, Chelsea College, London, United Kingdom, discusses the effect of acoustical surface waves on liquid crystals coupled to the surface of a body. In that study a liquid crystal material was applied directly to the surface of a body and a sonic transducer was also coupled directly to the surface of the body. The transducer caused sonic energy to travel along the surface to the liquid crystal. When the liquid crystal was observed through crossed polars (i.e., polarizers oriented at 90' to each other) optical changes in the liquid crystal enabled them to visualize surface waves (stripes with a separation equivalent to the wave length of the surface wave). However, clear visualization was only obtained at low acoustical intensities. At higher acoustical intensities, the liquid crystal started to flow (this is sometimes referred to as acoustic streaming) and destroy the picture. See J. S. Sandhu et al., Proceedings Institute of Acoustic, Spring meeting 1980 (G.B.).

The literature includes technical papers and publications which deal with combining liquid crystal technology and ultrasonic technology for generation of holograms and for flaw detection.

There are also many U.S. patents which deal with similar technology. See for example, Dreyer, U.S. Pat. No. 3,597,054; Kessler, U.S. Pat. No. 3,707,323; Greggus, U.S. Pat. No. 3,831,434; and Brenden, U.S. Pat. No. 3,879,989 which are representative of the state of the art.

None of the liquid crystal/ultrasonic systems which are disclosed in the prior art literature as patents provide an acceptable image of the flaw or discontinuity so that the system can be used on a real-time basis.

It is therefore an object of this invention to provide an ultrasonic system which uses liquid crystals for inspecting bodies and in which the image is satisfactory and of a high quality.

These and other objects of this invention will become apparent from the following description and appended claims.

SUMMARY OF THE INVENTION

There is provided by this invention a system for non-destructive testing and inspecting bodies for flaws and discontinuities using ultrasonic and liquid crystal technology and which provides a high quality visual image.

The image is obtained by using a unique liquid crystal detector cell which includes a pair of covers, a peripheral spacer and a liquid crystal material positioned between the covers. Both of the covers are rigid and substantially acoustically transparent and at least one is optically transparent. The optically transparent cover is laminated although both covers may be laminated. This structure minimizes acoustic absorption and internal reflections and each cover and the cell as a whole has an acoustic impedence comparable to that of the surrounding medium within which it is used. Thus very little acoustic energy is lost and a high quality image is assured.

The laminated cover includes at least three layers with each of the layers having a thickness much much less than $\frac{1}{4}$ of the wave length of the sound passing through the layer.

Other features of the cell and the ultrasonic system are discussed hereinafter.

BRIEF DESCRIPTION OF THE DRAWINGS

FIG. 5 is a schematic view showing a detecting apparatus and an optical system using transmitted light;

FIG. 6 is a diagrammatic view of an acoustic reflector;

FIGS. 7A and 7B are schematic views showing the use of acoustic lenses in ultrasonic inspection systems utilizing transmitted and reflected light;

FIG. 8 is a schematic view showing a system for examining large bodies for discontinuities using an array of ultrasonic transducers;

DESCRIPTION OF THE PREFERRED EMBODIMENT

The System in General

Figure 1:
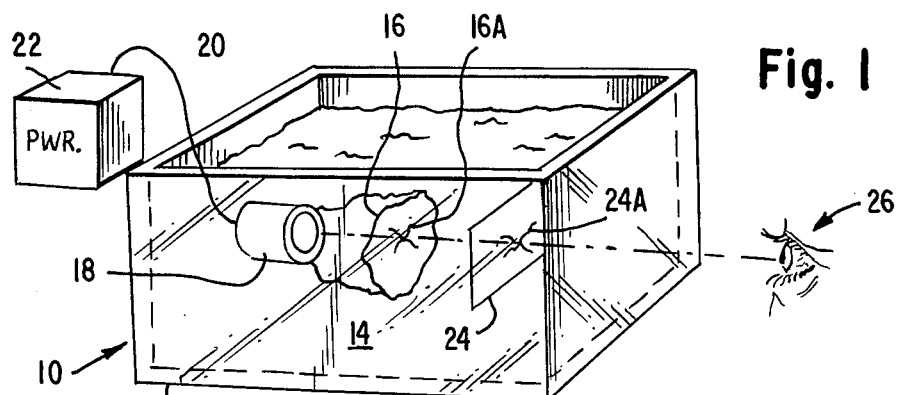
FIG. 1 is a diagrammatic view showing one embodiment of an apparatus for detecting discontinuities in a body.

Referring now to the drawings, there is generally shown in FIG. 1 a detection apparatus 10 which includes a transparent reservoir 12 containing a liquid 14, usually water. The body 16 which is to be inspected is immersed or partially suspended in the liquid. An ultrasonic transducer 18 is also immersed in the bath and connected via line 20 to an external power source 22. A liquid crystal detector 24 is also immersed in the liquid and is aligned with the transducer 18 and body 16. An observer 26 can thus view the liquid crystal detector 24 through the reservoir 12. An intentionally introduced x-shaped flaw 16A in the body 16 is shown as an image 24A on the cell 24.

In operation the transducer 18 emits ultrasonic energy which insonifies or sonically illuminates the body 16. The presence of the flaw modifies the uniform ultrasonic waves incident on the object so that the exiting waves are no longer uniform and carry information relating to the size, shape and position of the flaw. Thus the liquid crystal detector interacts selectively and is differentially excited.

In other words, the differing energy levels cause variations in the liquid crystal and optical differences in the detector. Thus, the image 24A is formed on the detector 24 and corresponds to the internal flaw or discontinuity 16A in the body. An observer 26 can immediately detect visually the differences in the image and thereby establish that there is a flaw or discontinuity in the body 16.

This procedure thus permits a real time observation of the discontinuity without the hazards associated with X-ray techniques or the time consumed in developing X-ray film. Similarly the cost and reliability questions associated with computer analysis and other electronic signal processing techniques are eliminated.

The foregoing embodiment is particularly adaptable to systems in which substantially planar bodies are to be inspected and in which the sonic energy can be transmitted through the body.

Figure 2:
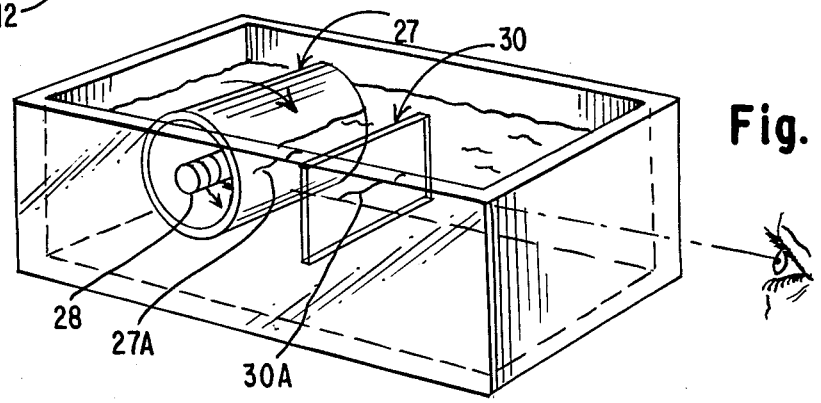
FIG. 2 is a diagrammatic view showing the use of the detection technique with a cylindrical body.

Referring now to FIG. 2, a hollow cylindrically shaped body 27 such as a pipe or tube is shown which is to be inspected. A transducer 28 which is of a cylindrical type is positioned within the cylinder for directing sonic energy radially outwardly toward the wall of the cylinder and the cylinder is rotated 360 degrees so that the entire body can be examined. If the transducer is shorter than the body so that the entire body cannot be examined in one revolution, the transducer can be placed in a first position; the body rotated 360 degrees; the transducer is then moved axially to a second position; and the body is rotated 360 degrees; and so forth until the cylinder has been fully examined. The liquid crystal detector 30 is positioned to receive the sonic energy transmitted from the transducer 28 through the cylinder 27. The detector is planar and a flaw such as 27A in the wall of the cylinder will appear as an image 30A on the liquid crystal detector.

Figure 3:
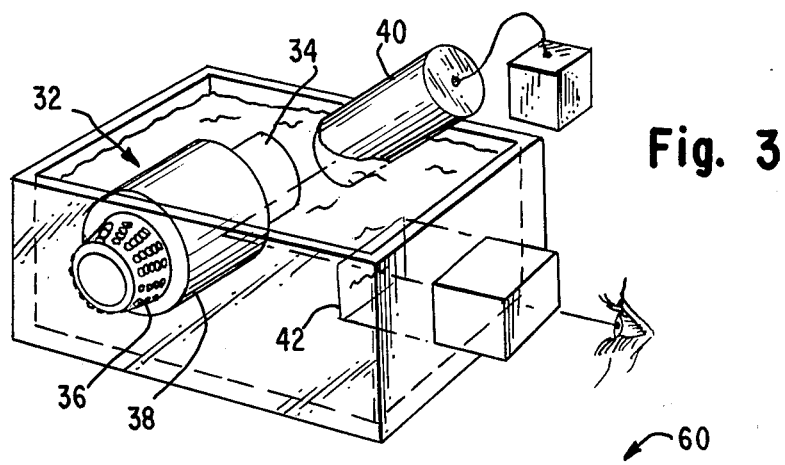
FIG. 3 is a diagrammatic view showing the apparatus when used to detect discontinuities in an oil drilling bit.

Referring now to FIG. 3 it is sometimes difficult to place an ultrasonic transducer at the center of a body due to some unusual geometric shape. In FIG. 3 there is shown an oil well drill bit 32. The drill bit includes a generally tubular or cylindrical end 34, cutting edges 36 and a bulbous intermediate section 38.

A reflection technique can be used in which a transducer 40 beams sonic energy towards the surface of the drill bit and a liquid crystal detector 42 is arranged to receive sonic energy reflected from the drill bit. As can be appreciated, the transducer 40 and the detector 42 are arranged at appropriate angles to one another to emit sonic energy and receive the reflected energy.

In addition to detecting flaws, such as cracks, inclusions or other discontinuities, the inner surface of a tubular member can be located. This is useful in determining the wall thickness of cylinders or other bodies.

The Optical Systems

Figure 4:
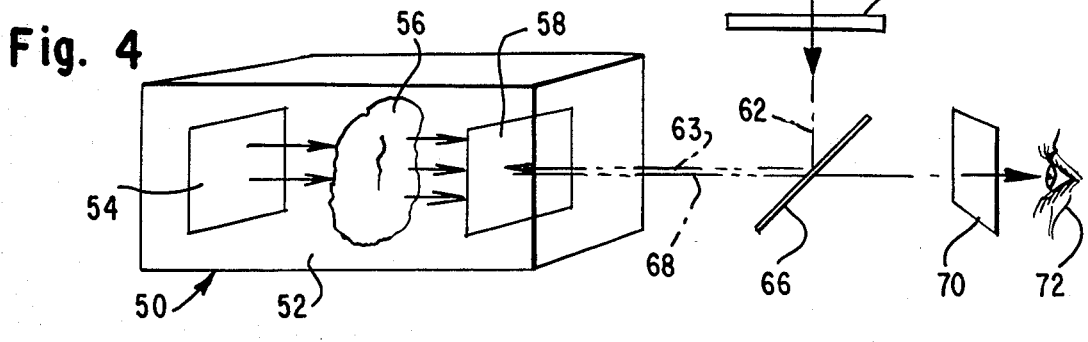
FIG. 4 is a schematic view showing a detecting apparatus and an optical system using reflected light.

Referring now to FIG. 4, there is shown a schematic representation of a system 50 for inspecting for discontinuities with an optical system that uses reflected light. The system includes a liquid bath 52 within which is positioned the ultrasonic transducer 54, an object 56 to be inspected and the liquid crystal detector 58. The optical portion of the system includes a light source 60 which radiates light along a path 62 and through a first polarizer 64. The light then strikes a half silvered mirror 66 and is reflected through the bath to the liquid crystal detector 58. Light is then reflected from the liquid crystal detector 58 along the path 68 through the half-silvered mirror and through a second polarizer 70 to the viewer 72. The first polarizer 64 and second polarizer 70 are oriented at 90' to each other and are sometimes referred to as crossed-polarizers.

In operation, the ultrasonic transducer 54 emits ultrasonic energy and insonifies the object 56 and the energy is transmitted through the object 56 to the liquid crystal detector 58 which selectively interacts with the detector so as to form an image corresponding to a discontinuity in the object. The detector is viewed using the optical system described above.

In FIG. 5 there is shown a apparatus for examining objects having discontinuity using an optical technique where light is transmitted through the liquid crystal cell. The system 80 includes an ultrasonic transducer 82, an object 84 to be examined, an acoustic reflector 86, and liquid crystal detector 87, all of which are immersed in a liquid bath. The acoustic reflector is also optically transparent and as shown in FIG. 6 can be triangularly shaped. The reflector has three sides 86A, 86B and 86C which define an internal air space. The side 86A can be made of a thin pane of glass, is acoustically reflective and optically transparent; the side 86B may be made of glass and must be optically transparent; and 86C need not be either optically transparent or acoustically reflective. In practice, the sides 86B and 86C were made of thick pieces of glass, whereas 86A was a thin pane of glass.

The acoustic properties of the water surrounding the reflector and the air inside the reflector are significantly different thus permitting reflection. The particular acoustical property is referred to as acoustic impedance which is defined by the expression $Z = \rho \times C$, where $\rho$ (rho) is density and C is the velocity of sound in the medium. Where there is a significant acoustic mismatch, there will be reflection.

Referring back to FIG. 5 the light source 88 emits a beam of light 90 which passes through a first polarizer 92, through the tank, through the acoustic reflector 86, through the detector 87, through the second polarizer 94 and then to the viewer 96. The polarizers 92 and 94 are oriented at 90' to each other.

In operation the transducer 82 emits sonic energy which insonifies the object 84 and the transmitted waves then pass to the reflector and are reflected from the reflector 86 to the detector. The light from the source 88 also passes through the reflector 86 (since it is optically transparent), to the liquid crystal cell 87 and thus the viewer 96 can readily see the image formed on the cell 87.

The reflected light technique, shown in FIG. 4, has the advantage that the liquid crystal cell 58 can be positioned close to the object 56 which is to be examined and thereby minimize energy absorption between the transducer, object and the cell thus permit the detection of small discontinuities by shadow imaging.

On the other hand, the transmitted light technique, shown in FIG. 5, has the advantage that a high contrast image can be obtained.

In determining which of the two techniques to use two factors are to be considered. First, absorption in the coupling medium is a function of the square of the frequency (f-squared) which means that as the distance between the transducer, cell and object increase, absorption increases. Absorption is reduced as the frequency is reduced. Obviously as the absorption increases, image quality decreases for a given ultrasonic frequency; however, intensity may be increased to offset absorption through the fluid.

On the other hand, the size of the discontinuity which can be detected in the object is limited by the wave length (wl) of the ultrasonic wave traveling in the object. The expression "$C = f \times wl$" defines the relationship between velocity, frequency and wave length. If the object is to be examined is aluminum the sonic velocity will be approximately 6,000 meters per second and the frequency can be varied between 1 and 10 megahertz (10 to the 6th cycles per second). The smallest discontinuity that can be located in a body is limited by the shortest wave length of energy traveling in that body. Thus in aluminum with sonic energy at a frequency of 10 megahertz, the smallest discontinuity that can be located is 600 micrometers. The foregoing analysis is applicable to other materials.

Therefore, when detection of small discontinuities is important, the reflected light technique can be used since higher frequencies and smaller wave lengths are available; whereas if larger discontinuities are present but higher contrast is necessary, the transmitted light technique can be used.

Acoustical Lenses

In each of FIGS. 7A and 7B there is shown an acoustical lens system which includes an ultrasonic transducer 110, a first or condenser acoustical lens 112, the object to be examined 114, second or objective lens 116 and a liquid crystal detector 118. The optical portion of the systems are either of the reflective type (FIG. 7A) or the transmissive type (FIG. 7A). In FIG. 7A the ultrasonic energy is emitted from the transducer 110 and is directed to the first lens 112 which acts like a condenser lens in a light microscope. The lenses 112 and 116 can be fabricated from polystyrene, Plexiglas or other materials commonly used for acoustic lenses because of good acoustic match with the surrounding medium (i.e., differences in acoustic impedance are small.) Using such a lens, the ultrasonic energy is directed to the object 114. Energy transmitted through the object 114 is received by the objective lens 116 and is focused on the liquid crystal detector 118 to form an image.

FIG. 7B is similar to FIG. 7A except that an acoustical reflector 119 is used.

Ultrasonic Scanning

When an object to be examined is large it may be necessary to scan the entire object in order to generate the image. This can be done with a single transducer which is moved in a scanning motion across the object, in the same manner as one would scan using a flashlight beam. However, a more effective arrangement is to have a series of fixed position transducers which are selectively operated so as to give the effect of scanning. Such an arrangement is normally referred to as an array.

Referring now to FIG. 8 there is an array of transducers 100 which are controlled by controller 102 and which selectively direct sonic energy at an object 104. Sonic energy passing through the object 104 is received on the liquid crystal detector 106. The optical portions of the system are not shown for simplicity.

The controls can operate the transducers sequentially beginning with the first and then successively downwardly. Only one transducer is operated at a time so as to avoid interference patterns. Thus transducer A is operated, then transducer B, then C, etc. When the last transducer in the sequence is reached, the topmost transducer A is then operated again. The timing of the operation of the transducers is sometimes referred to as frame rate and is related to the transient behavior, (i.e., rise and decay time) of the liquid crystal cell itself. Thus the image formed in the upper portion of the liquid crystal detector and resulting from the operation of the transducer A must not be allowed to degrade beyond a visually acceptable level before the transducer A is reactivated. Thus the timing for the control 102 is determined by the transient response of the liquid crystal cell.

Figure 9:
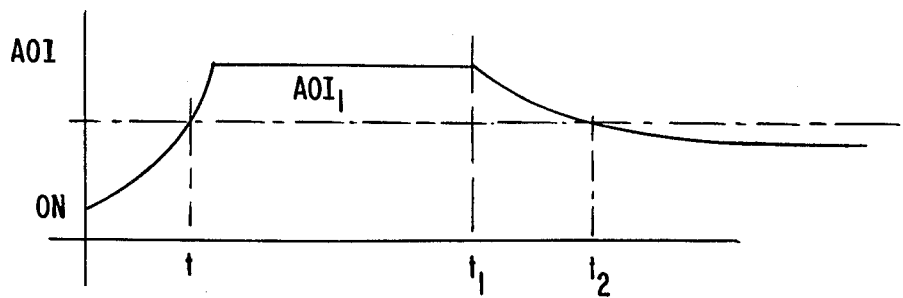
FIG. 9 is a graphic representation of the acoustic image characteristic for a liquid crystal material.

FIG. 9 shows a representative curve relating the quality of the acousto-optical image to time. It can be seen that from initiation, the quality of the image rises to a level, then remains constant until operation of the transducer is stopped and then image quality decays. If a minimally acceptable image is defined by the line "AO1" then the time period between deactivation of a transducer and reactivation of the same is depicted by the time between t1 and t2.

The control technology to affect the activating of the transducers is well known.

Turbulence Suppression

It is known that as the intensity of ultrasonic energy (acoustical intensity) directed toward a liquid crystal cell increases, turbulence within the cell increases and image quality decreases. It has been found that, the turbulence can be suppressed and image quality optimized, if an electrical field is applied to the liquid crystal cell.

In liquid crystal materials the dielectric constant is different in the parallel direction than in the perpendicular direction. This property is referred to as dielectric anisotropy. If the difference between the dielectric constant in the parallel direction and in the perpendicular direction is greater than zero, then turbulence will be suppressed. If the difference between the dielectric constants is less than zero, then sensitivity of the cell will be increased.

Figure 10:
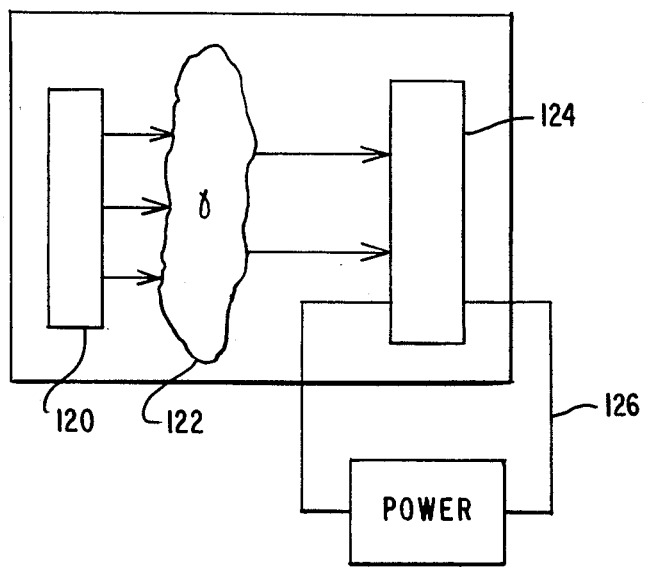
FIG. 10 is a schematic drawing showing the elements of a system for determining an acceptable image and using electric field improvement.

FIG. 10 shows in very simple form a system for applying electrical field to the cell. In this system, the transducer 120 directs ultrasonic energy to the object 122 and that energy is then received on the liquid crystal detector 124. In order to suppress turbulence and thereby optimize the image an electric field can be applied to the liquid crystal cell by a simple circuit as shown at 126. The current can be AC or DC but a low AC voltage is preferred, since the liquid crystal molecules are elongated and the difference in dielectric constants is positive, they may align themselves with the electric field. AC voltages are preferred since they minimize ion migration and other problems. In order to apply an electric field, electrically conductive but optically transparent films can be applied to internal cell surfaces and connected to an external power source.

Figure 11:
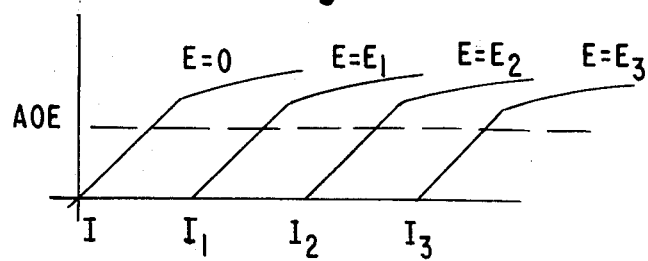
FIGS. 11 and 12 are graphic representations of the acoustic image, intensity and electric field relationships.

Experimentally a series of curves can be developed which will relate the electric energy to be applied for a particular ultrasonic intensity in order to obtain a desirable image. FIG. 11 shows a series of such curves where $E_1$, $E_2$, $E_3$ . . . represent different voltage levels.

Figure 12:
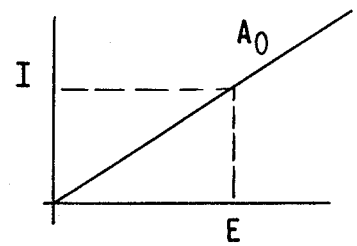

FIG. 12 shows an acceptable image line where for a given ultrasonic intensity it can be determined what electric energy is necessary to restore image quality.

Figure 13:
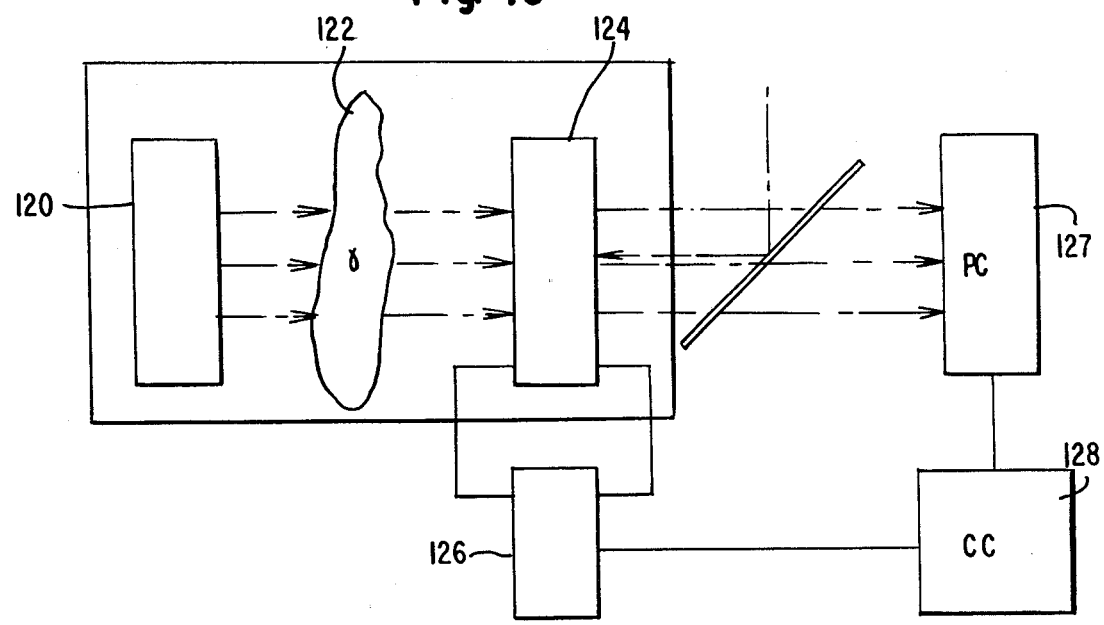
FIG. 13 is a schematic diagram of a servo control for automatically maintaining image quality.

FIG. 13 shows a schematic view of a servo system for automatically adjusting the electric field to assure a high quality image. This system, like that in FIG. 10, includes a transducer 120, an object 122, a detector 124 and circuit 126. In addition a photocell 127 is provided which measures the optical signal (reflected light) from the liquid crystal detector 124. The control circuit 128 couples the photocell 127 and circuit 120 so as to apply an electric field, in order to reduce turbulence and obtain the desired image quality.

Cell Construction

The liquid crystal cells used in the embodiments shown herein are constructed so as to assure a high quality image. In order to do so, certain constructional features are necessary.

Figure 14:
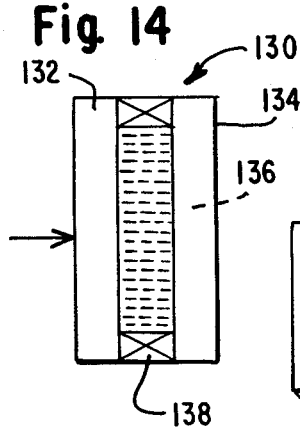
FIG. 14 is a cross-sectional view showing the preferred embodiment for a liquid crystal cell.

Referring now to FIG. 14, the detector or cell 130 is shown and the cell includes two outer covers 132 and 134, each of which are acoustically transparent, rigid and at least one of which is optically transparent. If a transmissive optical system as in FIG. 5 is used, then both covers must be optically transparent; but if a reflected light technique as in FIG. 4 is used, then only the cover on the observer side must be optically transparent. The liquid crystal material 136 is positioned between the covers and sealed in place by the use of a peripheral spacer 138.

The preferred liquid crystal material used in the cell of this invention is of the nematic type which is homeotropically aligned (i.e., molecules parallel to each other and normal to the cover surfaces).

Twisted nematic type liquid crystal cells may be used with small additions of cholesteric for example up to 0.03% by weight. Such twisted structures appear to quickly restore the cell to an initial condition after an impressed signal is removed. However the nematic type which is homeotropically aligned is preferred.

If the covers 132 and 134 are rigid, the liquid crystal molecules in the cell 136 are arranged perpendicular or normal to each of the covers 132 and 134. Such alignment is essential for proper operation of the cell. Furthermore, it is desirable that the liquid crystal material be of a uniform thickness and that the inner faces of each of the covers be parallel to each other.

It is also desirable that the cell be as transparent to sonic as possible. In other words, the sonic energy striking the surface of the cover 132 and transmitted through the entire cell should be maximized and the absorption and internal reflections minimized. Absorption or reflection of the energy will degrade image quality and sensitivity.

It is also desirable that the acoustical properties of the cell be very similar to the properties of the surrounding medium, usually water, so as to avoid any acoustic mismatch which causes the losses due to reflections, etc.

In analyzing this problem, it was determined that if the thickness of the cover was much much less than ¼ of the wave length of the sound wave propagating through the cover material (i.e., $w\frac{1}{4}$), then thickness effects relating to sonic absorption could be ignored for analytical purposes at normal incidence (i.e., the ultrasonic beam is perpendicular to the cover). For the optically transparent cover, glass has been used although other transparent materials may be used. In glass sound propagates at approximately 5,500 meters per second; thus at a frequency of 1 megahertz, $w\frac{1}{4}$ is equal to approximately 1,375 micrometers. Glass slides or panes are available in thicknesses of approximately 200 micrometers. Thus glass slides or layers are available in which the thickness of the layer can be effectively ignored for absorption purposes.

However, such thin slides are very flexible and would not assure the proper alignment of the liquid crystal molecules and uniform thickness of the liquid crystal layer.

It has been found that, in order to provide the desired rigidity, the glass cover must be a laminated structure having at least two glass panes.

Figure 15:
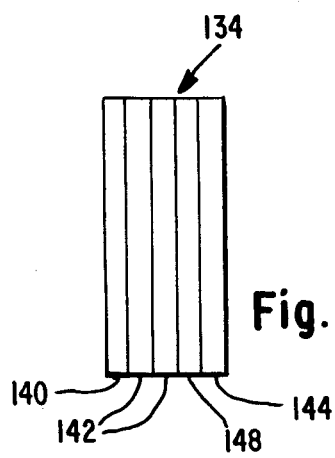
FIG. 15 is a diagrammatic view showing a laminated cover as for use in the detector.
Figure 16B:
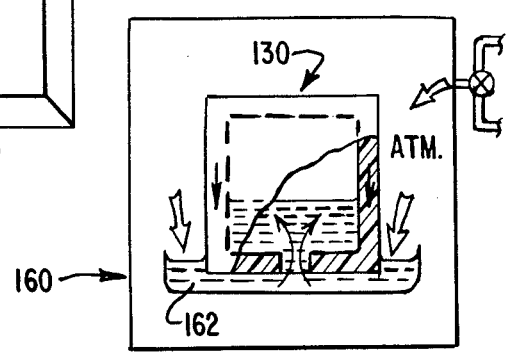

In FIG. 15, a five-layer thick glass cover is shown. The cover has three glass layers 140, 142 and 144, and two intermediate adhesive layers 146 and 148. Each of the layers is of a thickness very much less than the $w\frac{1}{4}$ for the appropriate material so that for absorption purposes the individual thicknesses can be ignored. The question is what is the acoustic impedance of the composite structure.

It has been suggested that an analysis similar to analysis for impedence in a parallel electric circuit could be used. Thus it has been empirically determined that the expression $1/Z_c = 1/Z_g + 1/Z_a + 1/Z_g + 1/Z_a + 1/Z_g \ldots$ can be used. $Z_c$ is the impedence of the composite, $Z_g$ the impedence of glass, and $Z_a$ is the impedence of the adhesive which is estimated to be similar to the impedence of Plexiglas or Lucite. Using such analysis, it has been determined that the impedance of the composite is very similar to that of water. For the purposes of calculating, the acoustic impedance of glass ($Z_a$) is approximately 11.42 and the acoustic impedance of adhesive ($Z_a$) is approximately 3.0. In this situation the composite impedance is approximately 1.1, and the impedence of water is 1.5. Therefore, a laminated structure having thin plates which make up a rigid cover can provide the desired rigidity and minimize absorption and reflection when waves enter along a line normal to the cover.

These laminated covers have been tested to determine what, if any, effect the angle of the incident beam to the cover has on ultrasonic transmission. This was done by placing a cover between a transmitting transducer and a receiving transducer and varying the angle of the cover relative to the direction of the ultrasonic beam. It has been found that there is very little change in transmission as the angle of the plate is changed with respect to the beam.

Therefore, a liquid crystal detector having laminated covers will have very little acoustic loss, very high transmission and will therefore maximize the sensitivity and image quality in the cell.

In terms of characteristics, the cell must have a pair of substrates with liquid crystal therebetween and have a peripheral spacer. A laminated cover must have at least three layers in order to assure rigidity, with each layer having a thickness much less than $w\frac{1}{4}$. Furthermore, the impedence of the laminated cover must approximate that of water, or the medium in which the cell is to be used, where the impedance of the composite is determined by the formula $1/Z_C = 1/Z_1 + 1/Z_2 + 1/Z_3 \ldots 1/Z_n$.

A cell 130 having laminated covers 132 and 134 can be used with either transmissive or reflected optical systems.

However, when using the reflected light optical system, the cover receiving the ultrasonic energy need not be optically transparent. Therefore, that cover need only be acoustically transparent. There are materials such as silicon and silicon carbide which have a very high sonic velocity and are very rigid. These materials can be formed in a single layer having a thickness which is much much less than $\frac{1}{4}$ of the wave length of the sound passing therethrough. These materials have been found to be sufficiently rigid to be useful as single layer cover. However, opaque laminated covers can be made and used if the need is present.

Therefore, in the reflected light system, the cover toward the viewer must be laminated and the cover facing the transducer may be a single rigid layer of a material such as silicon carbide or silicon. The single layer must still have a thickness much much less than $\frac{1}{4}$ of the wave length.

From the foregoing, it will be appreciated that cells having two laminated covers can be used with either reflected or transmissive optical system and cells having one laminated and one single thickness cover can be used only with the reflected light system.

Process for Filling the Cell

It will also be appreciated that in order to assure the highest quality image, the liquid crystal material 136 and the layer of adhesive 146 and 148 must be free of gas bubbles or entrained air.

In preparing the laminate, adhesive having a rubber-like texture is applied to the first layer, such as 140, and a second layer 142 is then secured to the adhesive so as to assure proper sealing. The adhesive may be a pressure sensitive material, such as known under the trade name Bostick, or may be a thermally sealable material.

Figure 14A:
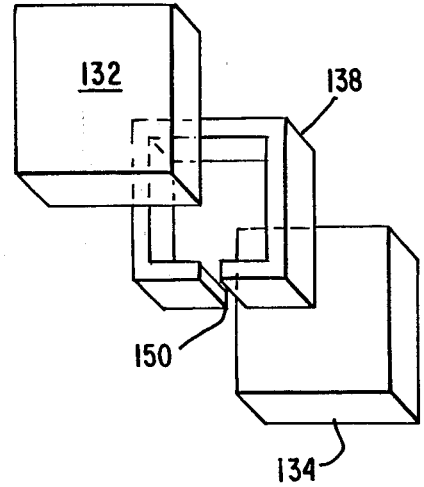
FIG. 14A is an exploded perspective view showing the elements of a liquid crystal detector cell.
Figure 16A:
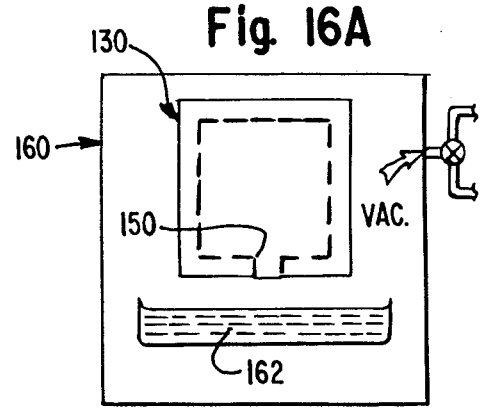
FIGS. 16A and 16B are diagrammatic views showing the manner in which a liquid crystal cell is filled.

In order to assure a gas-free liquid crystal, the cell is constructed with the peripheral spacer having an opening 150 thereon as shown in FIG. 14A. The cell is then placed in a vacuum chamber 160 and interior is evacuated. Thereafter, the cell is lowered into contact with the liquid crystal material 162 and the vacuum released. The release of the vacuum causes the liquid crystal material to flow into the cavity in the cell, thereby filling the cavity and then all that needs to be done is to plug the opening 150.

This cell construction has been found to provide an excellent image.

Actual cells have been constructed in which the liquid crystal layer is between about 100 and 300 micrometers thick. One hundred micrometers thick layers have been found to provide the best results.

Two different liquid crystal materials may be used. One is referred to as MBBA (methaoxy-benezyledene-butyl-aniline). In this material the dielectric anisotropy is less than zero. Another material which was found to be more suitable is referred to as biphenyl and is sold under the trade identification K15 and manufactured by a company known as BDH in Poole, Dorset, England. This material has dielectric anisotropy greater than zero, specifically +11. The glass layers forming the laminate are 200 micrometers thick and are secured together by a rubber-like adhesive in a relatively thin layer. The spacer is made of Mylar and is of the same thickness as the liquid crystal. Lecithin is mixed with the liquid crystal for alignment purposes. It would be desirable to dip the surfaces of the glass layers which contact the liquid crystal in lecithin, but if the laminate is already formed, the lecithin might react with the adhesive layers unless the exposed edges of the adhesive are suitably covered and protected.

If only an opaque single layer is necessary for cover, actual specimens have been made using silicon slides which were 200 micrometers thick. Cells 4 centimeters by 4 centimeters have been made and cells 10 centimeters by 10 centimeters can easily be prepared.

In actual testing washers, objects having a hollow cross, or hidden cross shape have been examined using this ultrasonic technique. When examining such parts, a piezoelectric transducer having a frequency response of about 2.25 megahertz have been used, usually with pulsed waves and the inner edges of the washer and cross could clearly be seen.

It will be appreciated that numerous changes and modifications can be made to the embodiment shown herein without departing from the spirit and scope of this invention.

What is claimed and desired to be secured by Letters Patent of the United States is:

1. A liquid-crystal acousto-optical detector cell for ultrasonic energy detection and image display said cell having a pair of substantially rigid covers, a liquid crystal material positioned between said covers, and a peripheral spacer and sealing member surrounding said liquid crystal material and sealingly engaging said covers, wherein the improvement comprises said cell exhibiting a good quality image, high sonic transmission and low angular dependence, and wherein
   (a) each of said covers is substantially acoustically transparent;
   (b) at least one of said covers is optically transparent and said optically transparent cover is a laminate having at least three layers, with each of said layers of said laminate having a thickness much much less than $\frac{1}{4}$ of the wave length of the ultrasonic energy propagating through said layer; and
   (c) with the other cover having at least one layer and the thickness of that layer being much much less than $\frac{1}{4}$ of the wave length of the ultrasonic energy propagating therethrough.

2. A cell as in claim 1 wherein each layer in each cover is much much less than $\frac{1}{4}$ the wave length of the ultrasonic energy propagating therethrough.

3. A cell as in claim 1, wherein the acoustical impedence of the cell approximates the acoustical impedence of a medium in which the cell is to be immersed.

4. A cell as in claim 3, wherein the acoustical impedence (Zc) of a laminated cover is approximated by the formula $$1/Zc = 1/Z1 + 1/Z2 - 1/Zn$$

where Z1–Zn is the acoustical impedance of each layer.

5. A cell as in claim 1, wherein said liquid crystal is a nematic liquid crystal homeotropically aligned.

6. A cell as in claim 5, wherein said liquid crystal material in a mixture of nematic and cholesteric, with there being 0.03 percent cholesteric by weight to form a twisted nematic cell.

7. A cell as in claim 4, wherein said layers include a glass layer, a rubber-like adhesive layer bonded thereto, and a glass layer bonded to said adhesive layer.

8. A cell as in claim 7, wherein each glass layer is approximately 200 micrometers thick.

9. A cell as in claim 8, wherein said cover has five layers and said layers are alternating glass, adhesive, glass, adhesive, glass.

10. A cell as in claim 1, wherein each of said covers is optically transparent and laminated.

11. A cell as in claim 1, wherein the cover is optically opaque and is fabricated of material selected from a group consisting of silicon carbide and silicon.

12. An ultrasonic system for inspecting a body and for detecting internal discontinuities, said apparatus comprising:
   (a) a liquid medium within which at least a portion of the body to be inspected is immersed;
   (b) ultrasonic transducer means for emitting and directing ultrasonic energy toward a body in said liquid medium;
   (c) a liquid-crystal acousto-optical detector cell for detecting ultrasonic energy passing through a body and image display, said cell having a pair of substantially rigid covers, a liquid crystal material positioned between said covers, and a peripheral spacer and sealing member surrounding said liquid crystal material and sealingly engaging said covers; and
   (d) an optical system for illuminating said liquid crystal cell so that images formed therein may be viewed wherein the improvement comprises;
   (e) said cell exhibits a good quality image, high sonic transmission and low angular dependence and wherein:
      (i) each of said covers is substantially acoustically transparent;
      (ii) at least one of said covers is optically transparent and said optically transparent cover is a laminate having at least three layers, with each of said layers of said laminate having a thickness less than $\frac{1}{4}$ of the wave length of the ultrasonic energy propagating through said layer; and
      (iii) with the other cover having at least one layer and the thickness of that layer being less than $\frac{1}{4}$ of the wave length of the ultrasonic energy propagating therethrough.

13. A system as in claim 12 wheein each layer in each cover is much much less than $\frac{1}{4}$ wave length of the ultrasonic energy propagating therethrough.

14. An ultrasonic system as in claim 12, wherein said optical system is of the reflected-light type and includes a light source, optic-reflector means and a viewing station, whereby light from said source is directed to said reflector, reflected to the optically-transparent cover of said cell and the image reflected therefrom to viewing position.

15. An ultrasonic system as in claim 13, wherein the other cover of said cell is optically opaque and is fabricated of a material selected from the group of silicon and silicon carbide having a thickness much much less than $\frac{1}{4}$ of the wave length of the sound propagating therethrough.

16. An ultrasonic system as in claim 14, wherein both of said covers are optically-transparent laminates.

17. An ultrasonic system as in claim 12, wherein said ultrasonic system further includes:
   sonic-reflector means for receiving sonic energy from a body being inspected and for reflecting said energy to said liquid crystal cell, said sonic reflector also being optically transparent at least in the direction of the reflected energy, and a transmissive-light optical system which includes a light source for directing light to and through said sonic reflector to said liquid crystal detector and a viewing station to view the image transmitted through said detector.

18. An ultrasonic system as in claim 17, wherein both covers of said cell are laminated and optically transparent.

19. An ultrasonic system as in claim 12, which further includes at least one sonic lens for receiving and focusing sonic energy, said lens being positioned in the sonic beam.

20. An ultrasonic system as in claim 12, wherein there is provided automatic means for applying an electric field to said cell to suppress turbulence due to sonic intensity by applying an electric field to said liquid crystal, said system comprising:

cell circuit means for applying a controlled electric field to said liquid crystal;

photocell means for receiving light energy from said detector and producing a voltage therefrom;

control circuit means coupled to said cell circuit means and said photocell for activating said circuit means to apply said field when the voltage from said cell drops below a predetermined value which corresponds to an image of an unacceptable quality.

21. An ultrasonic system as in claim 12, wherein there is further provided:

a plurality of transducers arranged in an array for selective operation to insonify the object, and controller means for selectively and sequentially activating and deactivating each of said transducers at a rate which will assure an image on said detector.

22. An ultrasonic system as in claim 12, wherein said body is an oil-drilling bit.

23. An ultrasonic system as in claim 12, wherein there is provided means for applying an electronic field to said cell to suppress turbulence due to sonic intensity by applying an electric field to said liquid crystal, said system comprising: cell circuit means for applying a controlled electric field to said liquid crystal.

* * * * *